United States Patent [19]

McLaughlin

[11] 4,443,635

[45] Apr. 17, 1984

[54] REMOVAL OF COLOR BODIES IN BISPHENOL PRODUCTION

[75] Inventor: William A. McLaughlin, Houston, Tex.

[73] Assignee: Shell Oil Company, Houston, Tex.

[21] Appl. No.: 447,056

[22] Filed: Dec. 6, 1982

[51] Int. Cl.$^3$ .................. C07C 39/16; C07C 37/68
[52] U.S. Cl. .................. 568/728; 568/724; 568/727
[58] Field of Search .................. 568/727, 728, 724

[56] References Cited

U.S. PATENT DOCUMENTS

| | | | |
|---|---|---|---|
| 1,977,627 | 10/1934 | Greenhalgh | 568/724 |
| 2,730,552 | 1/1956 | Williamson | 568/727 |
| 3,221,061 | 11/1965 | Grover et al. | 568/728 |
| 4,051,079 | 9/1977 | Melby | 260/2.2 R |
| 4,053,522 | 10/1977 | McClure et al. | 568/727 |
| 4,107,218 | 8/1978 | Konrad et al. | 560/724 |
| 4,169,211 | 9/1979 | Ligorati et al. | 568/724 |
| 4,191,843 | 3/1980 | Kwantes et al. | 568/724 |
| 4,308,404 | 12/1981 | Kwantes et al. | 568/727 |
| 4,308,405 | 12/1981 | Kwantes | 568/727 |
| 4,319,053 | 3/1982 | Heuser et al. | 568/727 |
| 4,354,046 | 10/1982 | Ladewig | 568/724 |
| 4,365,099 | 12/1982 | Faler et al. | 568/727 |
| 4,375,567 | 3/1983 | Faler | 568/724 |

FOREIGN PATENT DOCUMENTS

| | | | |
|---|---|---|---|
| 2048661 | 4/1972 | Fed. Rep. of Germany | 568/724 |
| 1373796 | 10/1964 | France | 568/724 |
| 1377227 | 12/1974 | United Kingdom | 568/724 |

Primary Examiner—Werren B. Lone
Attorney, Agent, or Firm—Ronald R. Reper

[57] ABSTRACT

In the production of bisphenols, color bodies which have been adsorbed on cationic exchange resins are removed by washing with at least one phenate selected from phenates of an alkali metal and of ammonia.

9 Claims, No Drawings

REMOVAL OF COLOR BODIES IN BISPHENOL PRODUCTION

BACKGROUND OF THE INVENTION

It is known to prepare bisphenols, e.g. bisphenol A, by continuously reacting in a reaction zone at least 2 moles of a phenol and a carbonyl compound in the presence of an acidic catalyst, such as hydrochloric acid, sulfuric acid or a cation-exchange resin. The reaction effluent, in addition to unreacted starting materials and the desired bisphenol product typically contains reaction by-products and color bodies. Exemplary processes are described e.g., in the U.S. Pat. Nos. 1,977,627, 2,730,552, 3,049,568, 4,053,522, 4,191,813, 4,308,404 and 4,308,405 incorporated herein by reference. Usually the desired bisphenol product is separated as an adduct with phenol, and the mother liquor which contains the condensation by-products is recycled to the principal reaction zone, or to a second reaction zone, for at least partial conversion to the desired bisphenol, as described e.g., in U.S. Pat. Nos. 3,049,569 and 3,221,061 incorporated herein by reference.

The bisphenol products of such processes are themselves starting materials in the production of materials such as epoxy resins, polycarbonates, polysulfones, and antioxidents. With the advance of technology employing these materials it has become increasingly important that the bisphenols be color-free, i.e., contain few, if any color bodies. Cation exchange resins have proven useful adsorbents for adsorbing color bodies from the mother liquor. However, such resin adsorbents have only limited adsorption capacity, and it is desirable to be able to effectively and efficiently wash the color bodies from the cation ion exchange resins to restore their utility. Regeneration procedures employing acidified phenol/water wash as described in U.S. Pat. No. 4,051,079 or employing a mixed phenol/water wash as described in U.S. Pat. No. 4,107,218 have been only partially effective. An improved process has now been found wherein the color bodies may be effectively removed by washing with an aqueous solution of certain phenates.

SUMMARY OF THE INVENTION

The present invention is an improved process for preparing a bisphenol by reacting at least 2 moles of a phenol with a carbonyl compound in a reaction zone in the presence of an acidic catalyst to produce a product mixture containing phenol, bisphenol, and color bodies and wherein the product mixture is separated into a bisphenol/phenol adduct and a mother liquor stream, wherein at least a portion of said mother liquor stream is contacted with an insoluble acidic cationic exchange resin for a period of time and at a temperature sufficient to reduce the content of color bodies contained in said mother liquor stream prior to recycling said mother liquor to said reaction zone, the improvement comprising periodically removing the adsorbed color bodies from said adsorbent by washing said adsorbent with an aqueous solution of at least one phenate selected from the group consisting of phenates of at least one alkali metal and of ammonia.

DESCRIPTION OF PREFERRED EMBODIMENTS

Phenols suitable for use in preparing the bisphenols have a reactive hydrogen preferably in the para-position relative to the phenolic hydroxyl groups. Such phenols may be substituted by one or more alkyl groups such as lower alkyl groups, e.g., methyl, ethyl or tertiary butyl groups, halogen atoms such as chlorine atoms, or other substituents which do not interfere with the carbonyl condensation reaction. Exemplary phenols include ortho- and meta-cresol; 2,6-dimethylphenol ortho-sec. butylphenol; 1,3,5 xylenol; tetramethylphenol; 2-methyl-6-tert. butylphenol, orthophenylphenol; ortho- and meta-chlorophenol, ortho-bromphenol; and 2,6-dichlorophenol. Most preferred is phenol.

The carbonyl compounds used in the process may be aldehydes, but preferably are ketones. Specific ketones include acetone, methyl ethyl ketone, methyl propyl ketone, methyl vinyl acetone, and especially acetophenone and cyclohexanone. Particularly preferred is acetone. The present invention is particularly suitable in the preparation of 2,2-bis(4-hydroxyphenyl)propane (Bisphenol A).

The acidic catalyst for the phenol-carbonyl condensation reaction may be hydrochloric acid, sulfuric acid, a solid perfluorinated polymer catalyst having pendant sulfonic groups which may be partially neutralized, or acidic ion exchange resins having a plurality of pendant sulfonic acid groups. Typically the reaction is conducted at a temperature from 40° to 95° C. The effluent from the phenol/carbonyl reaction contains unreacted starting materials, soluble catalyst if used, any promoter material such as methyl mercaptan, the desired bisphenol product, and by-products. After removal of volatile materials, the remaining reaction product is cooled to about 40° C. to 50° C. to form a crystalline adduct with phenol having a molar ratio of about 1:1 bisphenol to phenol. The adduct is then separated as crystals from the mother liquor and processed further to separate the phenol, e.g., by vacuum distillation, in order to recover the desired bisphenol product. The mother liquor, after separation of the adduct generally then is recycled either to the primary reaction zone or to a second reaction zone containing at least one bed of a cation exchanger.

The acidic cation exchangers are preferably strong acid ion exchange materials such as those resins and polymers having a plurality of pendant sulphonic groups. Exemplary are sulphonated polystyrene, poly(styrene-divinylbenzene) copolymers and sulphonated phenol-formaldehyde resins. Specific examples include Amberlite IR-120H, Amberlyst 15H, Dowex 50-X-4, Dowex MSC-1H, Duolite C-26, Permutit QH, Chempro C-20 and Imac C8P/H (Amberlite, Amberlyst, Dowex, Duolite, Permulite, Chempro and Imac are registered trademarks).

The exchange capacity of the acidic resin is preferably at least 2.0 meg $H^+/g$ of dry resin, with exchange capacities in the range of from about 3.0 to about 5.5 meg $H^+/g$ dry resin being particularly preferred.

The temperature of the adsorption bed is not critical and may vary with the range from about 40° C. to about 150° C., and preferably from about 40° C. to about 80° C. Temperatures lower than about 40° C. should be avoided as there is a risk that the phenol in the mother liquor may avoided as there is a risk that the phenol in the mother liquor may freeze. The contact rate of the mother liquor through the adsorption bed or beds may vary between wide limits. For example, the liquid hourly space velocity (LHSV) of the mother liquor may vary in the range from about 0.2 to 20 liters mother liquor. liter adsorbent$^{-1}$. hour$^{-1}$. The adsorption zone may comprise a single adsorption bed or two or more beds in series. For continuous operation it will be advantageous to employ beds arranged in parallel to alternately flow the mother liquor through one side and regenerate the other.

The adsorbed color bodies can be desorbed from the acidic cationic exchange resin bed by an aqueous phenate wash containing at least one phenate of an alkali metal or ammonia. Examples include sodium phenate, potassium phenate, lithium phenate, Rubidium phenate, and cesium phenate. Sodium phenate, potassium phenate and ammonium phenate are preferred as less costly. The amount of phenate is not critical with amounts from about 1 to 7 times and preferably 2 to 6 times the exchange capacity of the resin being suitable. The aqueous phenate wash solution should have a ph of at least about 8, and preferably at least about 10. Phenate wash solution having a ph in the range from about 10.5 to about 11.6 has been found most effective. The use of phenate wash solutions having a ph above about 11.6 is effective but adds to the expense of the regeneration procedure. The aqueous phenate wash can contain from about 10% to about 70%, preferably from about 25 to about 65% and most preferably about 30 to about 60% by weight of phenate. Preferably, after the adsorbent has been phenate washed, it is activated by passing therethrough a strong acid in an amount in excess of the stoichiometric amount equivalent to the exchange capacity of the resin. Any strong acid such as p-toluene sulfonic acid may be used; mineral acids such as sulfuric acid, and phosphoric acid, are preferred and hydrochloric acid is particularly preferred. The amount of acid is not critical, with amounts from about 1.1 to 5 times the exchange capacity of the resin being very suitable.

It should be noted that phenates have been described as useful catalysts for the condensation reaction of monohydric mononuclear phenols with ketones, see e.g., U.S. Pat. No. 2,858,342, however, such chemistry is not dominant in the instant process since the mother liquor when contacting the resin adsorbent, will have been substantially freed of ketone in earlier conventional devolatilization step prior to filtration of the phenol-bisphenol A adduct, from which filtration step the mother liquor is obtained.

The invention is further illustrated by means of the following Illustrative Embodiments which are given for the purpose of illustration only, and the invention is not to be regarded as limited to any specific materials or conditions herein.

In Illustrative Embodiments I-VI, a tubular column having a 1 cm internal diameter was partially filled with a spent macroreticular strong acid cation exchange resin which resin when fresh is commercially available under the tradename "DOWEX MSC1". The spent resin adsorbent had treated about 900 bed volumes of a mother liquor from a commercial Bisphenol A process wherein acetone and phenol are converted in the presence of a hydrochloric acid catalyst together with a lower alkyl thiol promoter. The mother liquor represents that liquid part of the reaction product after devolatilization and filtration separation of a solid bisphenol Aphenol adduct. The resin which when fresh (unused) was originally a light amber color was now a dull black.

The effectiveness of the resin adsorbent to remove color bodies from the mother liquor had fallen from about 95% color removal after 50 bed volumes of mother liquor to virtually no color removal after 900 bed volumes. Color of the mother liquor before and after the resin adsorbent was determined by first allowing each sample to cool and solidify, then melting the samples and diluting the methanol to 50% volume. The concentration of color is measured with a photoelectric colorimeter. A blue broad band pass filter (420 nm) was used in the colormeter. The photoelectric colorimeter is read in terms of APHA PT/CO color numbers.

ILLUSTRATIVE EMBODIMENT I (COMPARATIVE)

The spent resin in the tubular column having a bed volume of approximately 10 cubic centimeters is treated with 200-300 bed volumes of a mixture of phenol 80% wt. and water 20% wt at a temperature of 55° C. and liquid hourly space velocity of 2 hr$^{-1}$ in an attempt to regenerate the resin. The capacity of this treated resin to remove color from additional mother liquor was only slightly restored.

ILLUSTRATIVE EMBODIMENTS II-VI (COMPARATIVE)

The procedure of Illustrative Embodiment I was repeated with a variety of agents and wherein after each treatment of a fresh sample of spent resin, the resin remained substantially colored. As shown in Table I, these attempted regeneration procedures were only partially effective.

TABLE I

Regeneration of Spent Resin

| Illustrative Embodiment | Solution | Bed Volumes | Initial Color Removal[a] |
|---|---|---|---|
| II | 0.2N HCl | 5 | 9% |
|  | H$_2$O | 2 |  |
| III | phenol/TFA[b] (4/1) | 5 | 67% |
|  | phenol | 2 |  |
|  | TFA | 5 |  |
|  | H$_2$O | 2 |  |
| IV | phenol/TFA (4/1) | 5 | 53% |
|  | phenol | 2 |  |
| V | TFA | 4 | 14% |
|  | H$_2$O | 15 |  |
| VI | 0.2N NaOH | 12 | 12% |
|  | H$_2$O | 2 |  |
|  | 0.2N HCl | 5 |  |
|  | H$_2$O | 3 |  |

[a]Mother liquor was passed over "regenerated" resin at 55° C. and LHSV 2 hr$^{-1}$. The fifth bed volume was analyzed for color and compared with the feed color. Initial Color Removal = (100%) (initial color minus color of fifth bed volume divided by the initial color)
[b]TFA = Trifluoroacetic acid

ILLUSTRATIVE EMBODIMENT VII (ACCORDING TO THE INVENTION)

The procedure of Illustrative Embodiment I is repeated except that the washing solution was only 2 bed volumes of approximately 50% by weight aqueous sodium phenate and the temperature was room temperature i.e. about 25° C. This phenate solution had been prepared by neutralizing phenol (99.5+% pure) with sodium hydroxide pellets to a final ph of 11.4. The dark color bodies were essentially stripped from the spent resin. The phenate solution was washed from the column with 2 bed volumes of deionized water resulting that the regenerated resin was substantially restored to the appearance of unused resin.

ILLUSTRATIVE EMBODIMENT VIII (ACCORDING TO THE INVENTION)

The procedure of Illustrative Embodiment VII is repeated except that the wash solution is a 60% wt solution of ammonium phenate (ph 10-11). After 2 bed volumes of ammonium phenate and two bed volumes of deionized water, the color bodies were essentially washed from the resin.

ILLUSTRATIVE EMBODIMENT IXI (ACCORDING TO THE INVENTION)

In order to verify the effectiveness of the regeneration method according to the invention under simulated commercial conditions a teflon lined, jacketed column of Hastelloy B (10.2 CM × 183 CM) was first loaded with fresh strong acid cationic exchange resin Duolite C26 TR. The resin bed having a volume of approximately 10.86 liters was first washed nine times with hot water (plant condensate) in increments of about one bed volume each to assure removal of any residual impurities from resin manufacture. Mother liquor from a commercial Bisphenol A process as described in Illustrative Embodiment I was passed continuously through the bed. The temperature of the mother liquor for the first 250 bed volumes was about 71° C. and then was reduced to about 60° C. Flow of the mother liquor was stopped after about 650 bed volumes of throughput owing to technical difficulties not associated with the resin column. After a delay of several weeks, the flow of mother liquor was reestablished and the bed was taken out of service after about 1200 bed volumes of total throughput. The performance of the bed to remove color fluctuated widely after the first 650 bed volumes. Accordingly the performance of the bed for only the first 650 volumes is compared to the performance of this resin after regeneration according to the invention.

To regenerate the resin bed, the column jacket was heated with warm water (52° C.) and residual mother liquor was drained off. The spent resin bed was soaked six times in successive batches of 50% w sodium phenate in water. The soaking period was about 30 minutes for each batch. The color of the resin after the second soak appeared to be similar to that of fresh resin, however, additional color was observed in the effluent from the second to the sixth soak. The bed was then washed with about 12 bed volumes of cold water. The washed resin was reacidified with 2 N aqueous hydrochloric acid in an amount twice the stoichiometric amount of the resin. The re-acidified resin was then washed with cold water until free of chloride (none detected with silver nitrate). Then the flow of mother liquor was restored to the now regenerated bed of resin adsorbent. The color of the first couple of bed volumes of treated mother liquor eluted from the adsorbent bed was actually darker than the mother liquor feed, but afterwards more than 90% of the color in the untreated mother liquor was being removed by the regenerated resin adsorbent. Overall color removal performance of the regenerated resin was substantially that of fresh resin at similar throughput of mother liquor.

I claim:

1. In a process for preparing bisphenols by reacting at least 2 moles of a phenol with a carbonyl compound in a reaction zone in the presence of an acidic catalyst to produce a product mixture containing phenol, bisphenol, and color bodies and wherein the product mixture is separated into a bisphenol/phenol adduct and a mother liquor stream, wherein at least a portion of said mother liquor stream is contacted with an insoluble acidic cationic exchange resin for a period of time and at a temperature sufficient to reduce the content of color bodies contained in said mother liquor stream prior to recycling said mother liquor to said reaction zone, the improvement comprising periodically removing the adsorbed color bodies from said adsorbent by washing said adsorbent with an aqueous solution having a pH of at least about 8 and containing from about 10 to about 70% by weight of at least one phenate selected from the group consisting of phenates of alkali metals and of ammonia.

2. The process of claim 1 wherein said solution contains from about 25 to about 65% by weight of phenate.

3. The process of claim 1 comprising the additional step after the adsorbent has been phenate washed, of activating the adsorbent by passing therethrough with a strong acid in an amount in excess of the stoichiometric amount equivalent to the exchange capacity of the resin.

4. A process as in claim 1 wherein the phenate is selected sodium phenate, potassium phenate and ammonium phenate.

5. A process as in claim 3 wherein the amount of acid is from about 1.1 to 5 times the exchange capacity of the resin.

6. A process as in claim 4 wherein the acid is a mineral acid.

7. A process as in claim 6 wherein the acid is selected from the group of hydrochloric acid, sulfuric acid, and phosphoric acid.

8. A process as in claim 1 wherein the bisphenol is prepared by reacting a phenol from the group consisting of phenol, ortho-cresol and meta-cresol.

9. A process as in claim 1 wherein the carbonyl compound is selected from the group consisting of acetone, acetophenone, and cyclohexanone.

* * * * *